(12) United States Patent
Wabl et al.

(10) Patent No.: US 6,528,284 B1
(45) Date of Patent: Mar. 4, 2003

(54) POLYNUCLEOTIDES ENCODING PROTEINS MEDIATING SWITCH RECOMBINATION

(75) Inventors: Matthias Wabl, San Francisco, CA (US); Rolf Jessberger, Rheinfelden (DE)

(73) Assignees: F. Hoffman La Roche, Ltd., Basel (CH); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/462,951
(22) PCT Filed: Jul. 16, 1998
(86) PCT No.: PCT/IB98/01191
§ 371 (c)(1), (2), (4) Date: Jan. 14, 2000
(87) PCT Pub. No.: WO99/03991
PCT Pub. Date: Jan. 28, 1999

(30) Foreign Application Priority Data

| Jul. 18, 1997 | (EP) | 97112326 |
| Jan. 15, 1999 | (IE) | 990033 |
| Sep. 20, 1999 | (IE) | 990782 |

(51) Int. Cl.[7] ............ C12N 15/12; C12N 15/63; C12N 5/10
(52) U.S. Cl. ............ 435/69.1; 435/71.1; 435/71.2; 435/252.3; 435/252.44; 435/320.1; 435/325; 435/254.2; 435/348; 435/471; 536/23.5; 530/350
(58) Field of Search ............ 536/23.1, 23.5; 530/350; 435/69.1, 71.1, 71.2, 471, 325, 252.3, 252.44, 320.1, 254.21, 348

(56) References Cited

U.S. PATENT DOCUMENTS 5,948,676 A * 9/1999 Chang et al. ............ 435/325

OTHER PUBLICATIONS

Borggrefe et al., "A B–specific DNA Recombination Complex," *J. Biological Chemistry*, 273(27): 17025–17035 (1998).

Hillier et al., "Pancreatic islet Homo sapiens clone 328253 (AC W39285)," *EMBL Sequence Database*, Heidelberg, Germany, May 17, 1996.

Jessberger et al., "A Mammalian Protein Complex That Repairs Double–Strand Breaks and Deletions by Recombination," *J. Biological Chemistry*, 268(20): 15070–15079 (1993).

Marra et al., "Mus musculus cDNA clone 819985 (AC AA437805)," *EMBL Sequence Database*, Heidelberg, Germany, Jun. 1, 1997.

* cited by examiner

*Primary Examiner*—Prema Mertz
(74) *Attorney, Agent, or Firm*—Paula A. Borden; Bozicevic, Field & Francis, LLP

(57) ABSTRACT

The present invention provides isolated SRTA-70 proteins that mediate immunoglobulin class switch recombination in antibody-producing cells, and methods of procuding such proteins. The invention further provides isolated polynucleotides encoding SRTA-70 proteins, as well as vectors and host cells comprising the polynucleotides. The invention further provides methods of using SRTA-70 proteins to identify agents that modulate immunoglobulin class switch.

11 Claims, 8 Drawing Sheets

Figure 1:
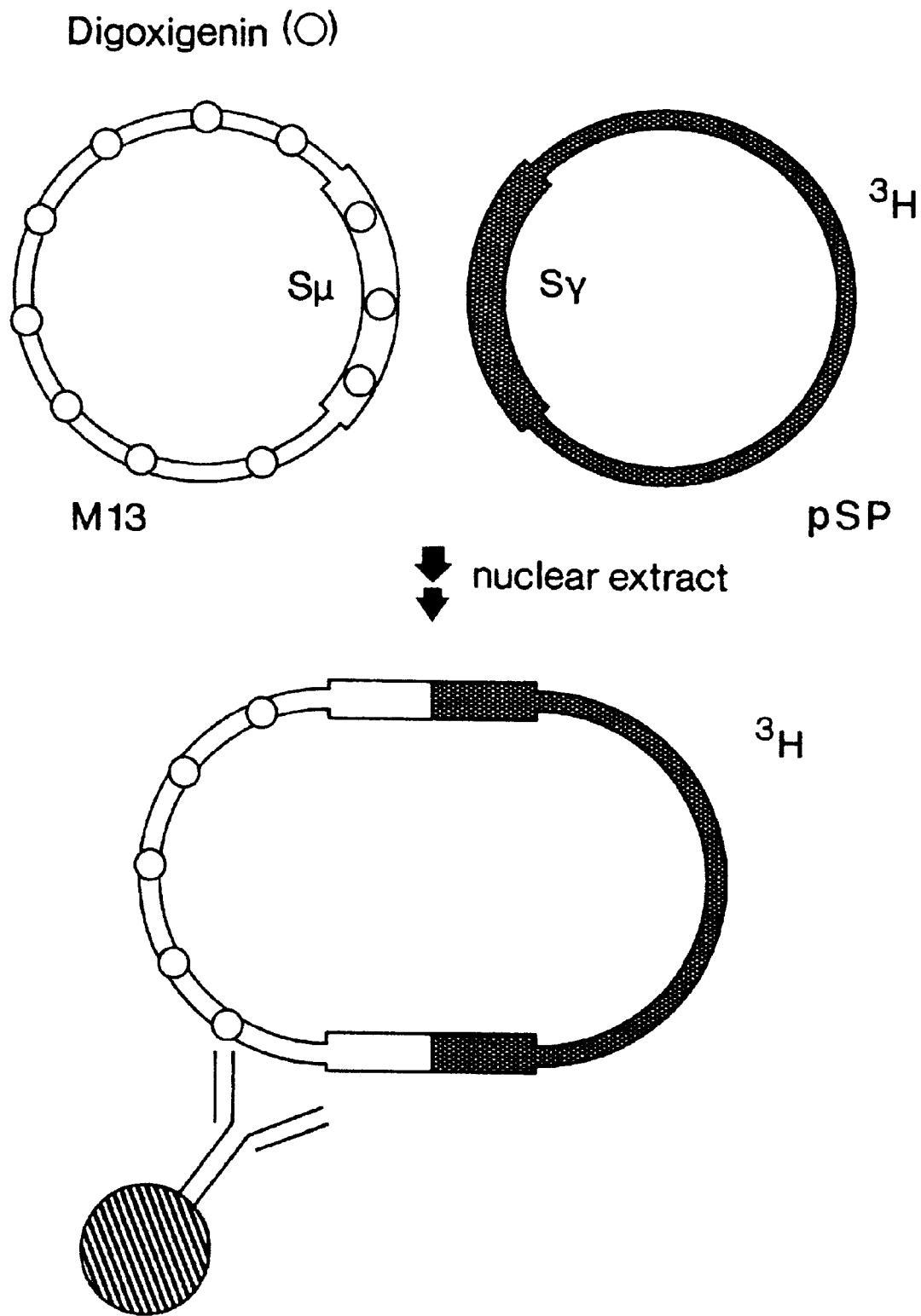

FIG. 3A
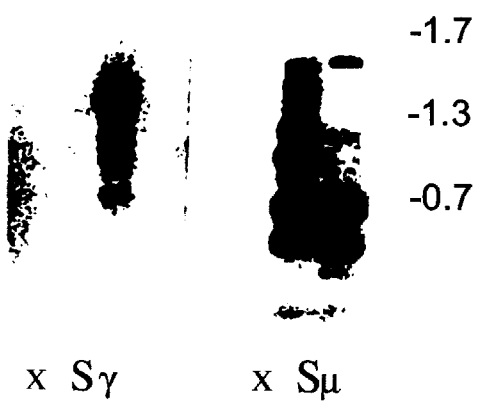
FIG. 3B
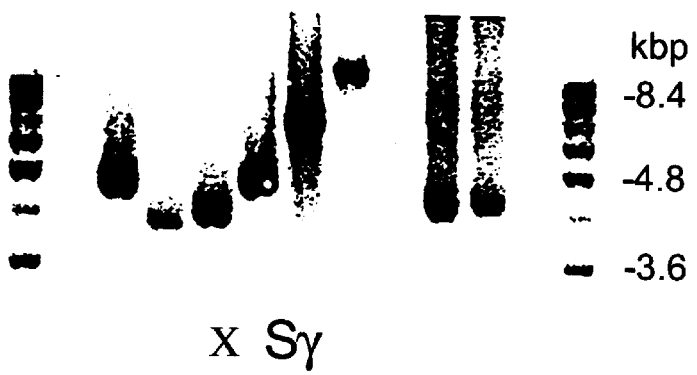
x Sγ
x Sμ

FIG. 4

```
   1  ATGAGGGGGTTGAAAGACGAACTGCTCAAAGCCATTTGGCACGCCTTCACCGCGCTCGAC
      M  R  G  L  K  D  E  L  L  K  A  I  W  H  A  F  T  A  L  D    20
  61  CTGGACCGCAGCGGCAAGGTCTCCAAGTCGCAACTCAAGGTCCTTTCCCATAACCTGTGC
      L  D  R  S  G  K  V  S  K  S  Q  L  K  V  L  S  H  N  L  C    40
 121  ACGGTGCTGAAGGTTCCACATGACCCGGTTGCCCTTGAGGAGCACTTTAGGGATGACGAT
      T  V  L  K  V  P  H  D  P  V  A  L  E  E  H  F  R  D  D  D    60
 181  GAGGGGCCTGTCTCCAATCAGGGCTACATGCCATATTTAAACAAGTTCATTTTGGAAAAG
      E  G  P  V  S  N  Q  G  Y  M  P  Y  L  N  K  F  I  L  E  K    80
 241  GTCCAAGACAACTTTGACAAGATTGAATTCAATAGAATGTGTTGGACACTTTGTGTCAAG
      V  Q  D  N  F  D  K  I  E  F  N  R  M  C  W  T  L  C  V  K   100
 301  AAAAACCTCACAAAGAGTCCTCTACTCATTACAGAAGATGATGCATTTAAAGTGTGGGTC
      K  N  L  T  K  S  P  L  L  I  T  E  D  D  A  F  K  V  W  V   120
 361  ATTTTCAACTTTTTGTCAGAGGACAAGTATCCACTAATTATTGTGCCAGAAGAGATTGAA
      I  F  N  F  L  S  E  D  K  Y  P  L  I  I  V  P  E  E  I  E   140
 421  TACCTGCTTAAGAAGCTTACAGAAGCTATGGGAGGAGGTTGGCAACAAGAACAATTTGAA
      Y  L  L  K  K  L  T  E  A  M  G  G  G  W  Q  Q  E  Q  F  E   160
 481  CATTACAAAATAAACTTTGATGACAATAAAGATGGCCTTTCTGCATGGGAACTTATTGAG
      H  Y  K  I  N  F  D  D  N  K  D  G  L  S  A  W  E  L  I  E   180
 541  CTAATTGGGAATGGACAGTTTAGCAAGGGCATGGACCGTCAGACCGTATCTATGGCCATT
      L  I  G  N  G  Q  F  S  K  G  M  D  R  Q  T  V  S  M  A  I   200
 601  AACGAAGTCTTCAATGAGCTTATTTTAGATGTATTGAAGCAGGGTTACATGATGAAGAAA
      N  E  V  F  N  E  L  I  L  D  V  L  K  Q  G  Y  M  M  K  K   220
 661  GGTCACAAACGGAAAAACTGGACTGAGCGCTGGTTTGTATTAAAACCCAACATAATTTCC
      G  H  K  R  K  N  W  T  E  R  W  F  V  L  K  P  N  I  I  S   240
 721  TACTATGTGAGCGAGGATCTGAAAGATAAGAAAGGAGACATCCTGCTGGATGAAAACTGC
      Y  Y  V  S  E  D  L  K  D  K  K  G  D  I  L  L  D  E  N  C   260
 781  TGTGTGGAGTCTCTGCCTGACAAAGATGGAAAGAAATGTCTTTTTCTAATAAAATGCTTT
      C  V  E  S  L  P  D  K  D  G  K  K  C  L  F  L  I  K  C  F   280
 841  GATAAGACCTTTGAAATCAGTGCCTCAGATAAGAAGAAGAAACAAGAATGGATTCAGGCC
      D  K  T  F  E  I  S  A  S  D  K  K  K  K  Q  E  W  I  Q  A   300
 901  ATTTACTCCACCATCCATCTGTTGAAGCTGGGCAGCCCCCCACCACACAAGGAAGCCCGC
      I  Y  S  T  I  H  L  L  K  L  G  S  P  P  P  H  K  E  A  R   320
 961  CAGCGTCGGAAAGAGCTCCGAAGGAAGCTGCTAGCCGAGCAGGAGGAGCTGGAGCGgCAG
      Q  R  R  K  E  L  R  R  K  L  L  A  E  Q  E  E  L  E  R  Q   340
1021  ATGAAGGAACTCCAAGCCGCCAATGAAAACAAGCAACAGGAGCTGGAAAGCGTGAGGAAG
      M  K  E  L  Q  A  A  N  E  N  K  Q  Q  E  L  E  S  V  R  K   360
1081  AAACTGGAGGAAGCAGCCTCTCGTGCGGCAGACGAGGAAAAGAAACGCTTGCAGACTCAG
      K  L  E  E  A  A  S  R  A  A  D  E  E  K  K  R  L  Q  T  Q   380
1141  GTGGAGCTACAGACCAGGTTCAGCACGGAGCTGGAGCGGGAGAAGCTGATCAGACAGCAG
      V  E  L  Q  T  R  F  S  T  E  L  E  R  E  K  L  I  R  Q  Q   400
1201  ATGGAGGAGCAGGTTGCCCAGAAGTCCTCCGAACTGGAGCAGTATCTGCAGCGAGTTCGG
      M  E  E  Q  V  A  Q  K  S  S  E  L  E  Q  Y  L  Q  R  V  R   420
1261  GAGCTGGAAGACATGTACCTAAAGCTGCAGGAGGCTCTTGAGGACGAGAGGCAGGCCCGG
      E  L  E  D  M  Y  L  K  L  Q  E  A  L  E  D  E  R  Q  A  R   440
1321  CAGGATGAAGAGACTGTGCGCAAGCTTCAGGCCAGGTTGCTGGAGGAAGAGTCTTCTAAG
      Q  D  E  E  T  V  R  K  L  Q  A  R  L  L  E  E  E  S  S  K   460
1381  AGGGCAGAGCTGGAAAAGTGGCACCTGGAGCAGCAGCAGGCCATTCAGACAACAGAGGCG
      R  A  E  L  E  K  W  H  L  E  Q  Q  Q  A  I  Q  T  T  E  A   480
1441  GAGAAGCAGGAGCTGGAACAGCAGCGTGTCATGAAGGAGCAGGCATTGCAGGAGGCCATG
      E  K  Q  E  L  E  Q  Q  R  V  M  K  E  Q  A  L  Q  E  A  M   500
1501  GCACAGCTGGAACAGTTGGAGTTGGAGCGGAAGCAGGCCCTGGAGCAGTATGAGGGAGTT
      A  Q  L  E  Q  L  E  L  E  R  K  Q  A  L  E  Q  Y  E  G  V   520
1561  AAAAAGAAGCTAGAGATGGCAACACATATGACCAAGAGCTGGAAGGACAAAGTGGCCCAT
      K  K  K  L  E  M  A  T  H  M  T  K  S  W  K  D  K  V  A  H   540
1621  CATGAGGGATTAATACGATTGATAGAACCAGGTTCCAAGAACCCTCATCTGATCACCAAC
      H  E  G  L  I  R  L  I  E  P  G  S  K  N  P  H  L  I  T  N   560
1681  TGGGGACCCGCAGCGTTCACCCAGGCAGAGCTCGAGGAGAGAGAGAAGAGCTGGAAAGAG
      W  G  P  A  A  F  T  Q  A  E  L  E  E  R  E  K  S  W  K  E   580
1741  AAGAAGACCACAGAGTGA  1758  (SEQ ID No:2)
      K  K  T  T  E  -      586   (SEQ ID No:1)
```

POLYNUCLEOTIDES ENCODING PROTEINS MEDIATING SWITCH RECOMBINATION

The present invention relates to the isolation, purification and characterization of proteins mediating switch recombination. The present invention further relates to the microbial production via recombinant DNA technology of recombination protein SRTA-70, a member of the proteins mediating switch recombination. The present invention further relates to the use of these proteins as therapeutically active agents in immune response modulation, specifically, in augmentation and suppression of the immune response.

Higher eukaryotes produce immunoglobulins (Ig) of diffent classes, which are defined by the constant region (C) of the heavy (H) chain. Upon stimulation by antigen expression of the early IgM class changes to that of another H chain class. This switch from one H chain class to another, named simply "class switching", occurs via DNA recombination. Switch recombination imprecisely joins two so-called switch (S) regions, which lie upstream of the H chain genes and contain highly repetitive sequences (for reviews see Esser and Radbruch, Annu. Rev. Immunol. 8, 717–735 [1990] and Harriman et al., Annu. Rev. Immunol. 11, 361–384 [1993]). The recombination mechanism for most class switching events can be described by the loop-excision model (Jäck et al., Proc. Natl. Acad. Sci. USA 85, 1581–1585 [1988]). The biochemistry of the class switch recombination process, however, remains largely unknown.

In order to study the mechanism of class switch recombination an assay that measures DNA-transfer activity was devised which makes use of two S (Sμ and Sγ2b) regions, cloned into two different, largely non-homologous vectors (FIG. 1). Using this assay three proteins in the S-Region Transfer Activity (SRTA) were identified: B23 (nucleophosmin), poly (ADP) ribose polymerase (PARP) and a novel 70-KDa protein SRTA-70.

Thus, in a first aspect of this invention, there are provided SRTA-70 proteins, specifically recombinantly produced SRTA-70 protein. The term "recombinantly produced SRTA-70 protein" refers to the protein of SEQ ID No. 1 or any protein or polypeptide having an amino acid sequence which is substantially homologous to the amino acid sequence SEQ ID No. 1 and further having the biological activities of the protein of SEQ ID No. 1.

As used hereinbefore the term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological activity and equivalent expression characteristics are considered substantially homologous. For purposes of determining homology, truncation of the sequence should be disregarded. Sequences having lesser degrees of homology, comparable bioactivity, and equivalent expression characteristics, e.g., fragments of the amino acid sequence SEQ ID No: 1 are considered substantial equivalents.

As used herein the term recombinantly produced SRTA-70 protein includes proteins modified deliberately, as for example, by addition of specific sequences that preferably bind to an affinity carrier material. Examples of such sequences are sequences containing at least two adjacent histidine residues (see in this respect European Patent No. 282 042). Such sequences bind selectively to nitrilotriacetic acid nickel chelate resins (Hochuli and Döbeli, Biol. Chem. Hoope-Seyler 368, 748 [1987]; European Patent No. 253 303). SRTA-70 proteins which contain such a specific sequence can, therefore, be separated selectively from the remaining polypeptides. The specific sequence can be linked either to the C-terminus or the N-terminus of the SRTA-70 protein.

There are further provided isolated DNA sequences encoding SRTA-70 proteins or fragments thereof. Specifically, the DNA sequences of this invention are defined to include the nucleotide sequence SEQ ID No: 2 or a fragment thereof or any DNA sequence which is substantially homologous to the nucleotide sequence SEQ ID No: 2 or a fragment thereof.

As used hereinbefore the term "substantially homologous", means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, DNA sequences having greater than 95 percent homology, encoding equivalent biological properties, and showing equivalent expression characteristics are considered substantially homologous. For purposes of determining homology, truncation of the DNA sequence should be disregarded. Sequences having lesser degrees of homology, encoding comparable bioactivity, and showing equivalent expression characteristics, e.g., fragments of the nucleotide sequence SEQ ID No: 2 are considered substantial equivalents. Generally, homologous DNA sequences can be identified by cross-hybridization under standard hybridization conditions of moderate stringency.

There are also provided vectors and expression vectors containing the DNA sequences of the present invention, hosts containing such vectors for the production of SRTA-70 proteins, and processes for the production of such DNA sequences, recombinant vectors and host cells.

Methods for the expression, isolation and purification of the SRTA-70 proteins are also provided.

The following steps outline the methods for recombinantly expressing the SRTA-70 proteins.

1) Cloning of DNA Sequences Encoding SRTA-70 Proteins

DNA sequences encoding SRTA-70 proteins can be cloned using a variety of techniques. Using the methods described in this application cDNAs encoding SRTA-70 proteins or fragments thereof can be produced. These cDNAs can be isolated and amplified by PCR technique using oligodeoxynucleotide DNA primers by conventional techniques.

The cDNA (SEQ ID No: 2) encoding the amino acid sequence SEQ ID No:1 is obtained using the DNA primers described in the examples. By using conventional technique, this cDNA has been isolated from a mouse spleen cDNA library.

The cDNA may be obtained not only from cDNA libraries, but by other conventional techniques, e.g., by cloning genomic DNA, or fragments thereof, purified from the desired cells. These procedures are described by Sambrook et al., in "DNA Cloning: A Practical Approach", Vol. I and II, D. N. Glover, ed., 1985, MRL Press, Ltd., Oxford, U. K.; Benton and Davis, Science 196, 180–182 [1977]; Grunstein and Hogness, Proc. Nat. Acad. Sci. 72, 3961–3965 [1975]; and Maniatis et al., in "Molecular Cloning-A Laboratory Manual", Cold Spring Harbor Laboratory [1989].

To obtain the cDNA encoding the SRTA-70 proteins cDNA libraries are screened by conventional DNA hybridization techniques by the methods of Benton and Davis, supra, or Grunstein and Hogness, supra, using radioactive SRTA-70 gene fragments. Clones which hybridize to the radioactive gene fragments are analyzed, e.g., by restriction endonuclease cleavage or agarose gel electrophoresis. After isolating several positive clones the positive insert of one clone is subcloned, e.g., into phagemids, and sequenced by conventional techniques.

Clones derived from genomic DNA may contain regulatory and intron DNA regions in addition to coding regions; clones derived from cDNA will not contain intron sequences. In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Whatever the source, the DNA sequence encoding SRTA-70 proteins may be molecularily cloned into a suitable vector for propagation of the DNA by methods known in the art. Any commercially available vector may be used. For example, the DNA may be inserted into a pBluescript SK⁻ vector. Appropriate vectors for use with bacterial hosts are described by Pouwels et al., in "Cloning Vectors: A Laboratory, Manual", 1985, Elsevier, N.Y. As a representative but nonlimiting example, useful cloning vectors for bacterial use can comprise a selectable marker and a bacterial origin of replication derived from commercially available plasmids which are in turn derived from the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA).

The DNA sequences encoding SRTA-70 proteins inserted in these commercially available vectors can be verified by methods known in the art, e.g., by standard nucleotide sequencing techniques.

DNA sequences that code for SRTA-70 proteins from mammals other than mice may be used herein. Accordingly, while specific DNA has been cloned and sequenced in relation to the DNA sequence in mouse cells, any mammalian or vertebrate cell potentially can be used as the nucleic acid source of the SRTA-70 protein.

2) Production of SRTA-70 Proteins

Cloned DNA sequences that code for SRTA-70 proteins can be expressed in hosts to enable the production of these proteins with greater efficiency. Techniques for these genetic manipulations are specific for the different available hosts and are known in the art.

For expression of SRTA-70 proteins in hosts, in principle, all vectors which replicate and express DNA sequences encoding the SRTA-70 proteins in the chosen host are suitable. Expression vectors suitable for use in prokaryotic host cells are mentioned, for example, in the textbooks "Molecular Cloning—A Laboratory Manual", Cold Spring Harbor Laboratory [1982] and [1989], of Maniatis et al. Examples of other vectors are plasmids of the pDS family (Bujard et al., Methods in Enzymology, eds. Wu and Grossmann, Academic Press, Inc., Vol. 155, 416–433 [1987]).

Such prokaryotic expression vectors which contain the DNA sequences coding for the SRTA-70 proteins operatively linked with an expression control sequence can be incorporated using conventional methods into any suitable prokaryotic host cell. The selection of a suitable prokaryotic host cell is determined by different factors which are well-known in the art. Thus, for example, compatibility with the chosen vector, toxicity of the expression product, expression characteristics, necessary biological safety precautions and costs play a role and a compromise between all of these factors must be found.

Suitable prokaryotic host organisms include gram-negative and gram-positive bacteria, for example *E. coli* and *B. subtilis* strains. Examples of prokaryotic host organisms are *E. coli* strain M15 (described as strain OZ 291 by Villarejo et al. in J. Bacteriol. 120, 466–474 [1974] and *E. coli* W3110 [ATCC No. 27325]). In addition to the aforementioned *E. coli* strains, however, other generally accessible *E. coli* strains such as *E. coli* 294 (ATCC No. 31446) and *E. coli* RR1 (ATCC No. 31343) can also be used. In a preferred embodiment of the present invention *E. coli* M15 is used as the host organism.

Expression vectors suitable for use in yeast cells are described in "Guide to yeast genetics and molecular biology", Guthrie and Fink, eds., Methods in Enzymology, Academic Press, Inc., Vol. 194 (1991) and "Gene expression technology", Goeddel, ed., Methods in Enzymology, Academic Press, Inc., Vol. 185 [1991]. Examples of suitable yeast cells are *Saccharomyces cerevisiae, Pichia pastoris, Hansenula polymorpha, Schizosaccharomyces pombe* cells. An overview on various yeast expression systems is given by Romanos et al., Yeast, Vol. 8, 423–488 [1992].

The transformation with the yeast expression vectors is carried out as described by Klebe et al., Gene, Vol. 25, 333–341 [1983].

Plants can also be used as hosts for the production of SRTA-70 protein of the present invention. Transfer of the DNA sequence coding for the SRTA-70 protein may be achieved by a variety of methods (for review see Potrykus and Spangenberg, eds., Gene transfer to plants. A laboratory manual, Springer Verlag, Heidelberg, Germany [1995]), whereby the DNA sequence for the SRTA-70 protein is integrated into the chromosome of the host plants. Overexpression of the SRTA-70 protein may be achieved, for example, by transforming a plant host with the DNA sequence coding for the SRTA-70 protein. Examples of plant hosts for the production of SRTA-70 protein include, but are not limited to maize (*Zea mays,* Ishida et al., Nature Biotechnology 14, 745–750 [1996]), flax (*Linum usitatissimum,* Dong and Mchughen, Plant Sci. 88 (1), 61–71 [1993]), soybean (*Glycine max,* Christou et al., Tibtech 8, 145–151 [1990]), alfalfa or tobacco.

The manner in which the expression of the SRTA-70 proteins is carried out depends on the chosen expression vector host cell system.

Usually, the prokaryotic host cells which contain a desired expression vector are grown under conditions which are optimal for the growth of the prokaryotic host cells. At the end of the exponential growth, when the increase in cell number per unit time decreases, the expression of the desired SRTA-70 protein is induced, i.e., the DNA coding for the desired SRTA-70 protein is transcribed and the transcribed mRNA is translated. The induction can be carried out by adding an inducer or a derepressor to the growth medium or by altering a physical parameter, e.g., a change in temperature. For example, the expression can be controlled by the lac repressor.

By adding isopropyl-β-D-thiogalactopyranoside (IPTG), the expression control sequence is derepressed and the synthesis of the desired protein is thereby induced.

The yeast host cells which contain a desired expression vector are grown under conditions which are optimal for the growth of the yeast host cells. A typical expression vector contains the promoter element, which mediates the transcription of mRNA, the protein coding sequence, a ribosomal binding site for effective translation. Additional elements may include terminator, signal, and upstream activating sequences.

The yeast cells are grown as described by Sherman in "Guide to yeast genetics and molecular biology", Guthrie and Fink, eds., Methods in Enzymology, Academic Press, Inc., Vol. 194, 3–21 [1991].

The baculovirus-insect cell vector system can also be used for the production of the SRTA-70 proteins of the present invention (for review see Luclow and Summers, Bio Technology 6, 47–55 [1988]). The SRTA-70 proteins produced in insect cells infected with recombinant baculovirus can undergo post-translational processing including but not limited to N-glycosylation (Smith et al., Proc. Nat. Scad. Sci. USA 82, 8404–8408) and O-glycosylation (Thomsen et al., 12. International Herpesvirus Workshop, University of Philadelphia, Pa.).

Mammalian cells can also be used as hosts for the recombinant production of SRTA-70 proteins. Suitable mammalian host cells include but are not limited to human Hela, H9 and Jurkat cells, mouse NIH3T3 and C127 cells, CV1 African green monkey kidney cells, quail QC1–3 cells, Chinese hamster ovary (CHO) cells, mouse L cells and the COS cell lines.

Expression vectors suitable for use in mammalian host cells include but are not limited to pBC12MI, pBC12BI, pSV2dhFr, p91023(B), pcDNA3, pcDV1, pRSVcat, pGA291, pGA293, pGA296, pBC12/HIV/IL-2 and PGA300. Such vectors are preferably introduced into suitable mammalian host cells by transfection.

Usually, the mammalian host cells which contain a desired expression vector are grown under conditions which are optimal for the growth of the mammalian host cells. A typical expression vector contains the promoter element, which mediates the transcription of mRNA, the protein coding sequence, and the signals required for efficient termination and polyadenylation of the transcript. Additional elements may include enhancers and intervening sequences bounded by spliced donor and acceptor sites.

Most of the vectors used for the transient expression of a given coding sequence carry the SV40 origin of replication, which allows them to replicate to high copy numbers in cells (e.g. COS cells) that constitutively express the T antigen required to initiate viral DNA synthesis. Transient expression is not limited to COS cells. Any mammalian cell line that can be transfected can be utilized for this purpose. Elements that control a high efficient transcription include the early or the late promoters from SV40 and the long terminal repeats (LTRs) from retroviruses, e.g. RSV, HIV, HTLVI. However, also cellular signals can be used (e.g. human β-actin-promoter).

Alternatively stable cell lines carrying a gene of interest integrated into the chromosome can be selected upon co-transfection with a selectable marker such as gpt, dhfr, neomycin or hygromycin.

Now, the transfected gene can be amplified to express large quantities of a foreign protein. The dihydrofolate reductase (DHFR) is a useful marker to develop lines of cells carrying more than 1000 copies of the gene of interest. The mammalian cells are grown in increasing amounts of methotrexate. Subsequently, when the methotrexate is withdrawn, cell lines contain the amplified gene integrated into the chromosome.

Transgenic animal vector systems can also be used for the production of SRTA-70 proteins of the present invention (for review see Pinkert, Transgenic animal technology: a laboratory handbook, Academic Press, San Diego [1993]). Using specific signal sequences the desired SRTA-70 protein can also be secreted into the milk of the animal (for examples see Drohan et al., J. Cell. Biochemistry 17a, 38–38 [1993]; Lee et al., Appl. Biochem. Biotechnol. 56, 211–222 [1996]) thus allowing the use of the milk as a source for SRTA-70 protein.

For the isolation of small amounts of SRTA-70 proteins expressed in prokaryotic host cells for analytical purposes, e.g., for polyacrylamide gel electrophoresis, the host cells can be disrupted by treatment with a detergent, e.g., sodium dodecyl sulphate (SDS). Larger quantities of SRTA-70 protein can be obtained by mechanical (Charm et al., Meth. Enzymol. 22, 476–556 [1971]), enzymatic (lysozyme treatment) or chemical (detergent treatment, urea or guanidinium hydrochloride treatment, etc.) treatments followed by use of known methods, e.g., by centrifugation at different gravities, precipitation with ammonium sulphate, dialysis (at normal pressure or at reduced pressure), preparative isoelectric focusing, preparative gel electrophoresis or by various chromatographic methods such as gel filtration, high performance liquid chromatography (HPLC), ion exchange chromatography, reverse phase chromatography and affinity chromatography (e.g., on Sepharose® Blue CL-6B).

Preferably, the SRTA-70 proteins expressed in prokaryotic host cells are obtained after Ni-Agarose affinity chromatography followed by gel filtration.

The SRTA-70 proteins expressed in mammalian host cells or in the baculovirus-insect cell vector system can be isolated from the host cell medium using standard protein purification methods.

The SRTA-70 proteins can be used as therapeutically active agents in immune response modulation, specifically, in augmentation and suppression of the immune system.

Furthermore, the SRTA-70 proteins can be used as mediators of protein-protein interactions to retrieve other proteins involved in DNA recombination and repair, especially class switch recombination, and other metabolic processes. SRTA-70 proteins can serve as hooks to pull other relevant proteins out of cell extracts, and allow cloning the respective genes. SRTA-70 proteins can also be used for identification of compounds inhibiting or boosting the function of SRTA-70 proteins and proteins and nucleic acids interacting with SRTA-70 proteins (agonists or antagonists).

Antibodies can also be raised against the SRTA-70 proteins of the present invention. These antibodies can be used in a well-known manner for diagnostic or therapeutic purposes as well as for localisation and purification purposes. Such antibodies can be produced by injecting a mammalian or avian animal with a sufficient amount of a vaccine formulation comprising a SRTA-70 protein of the present invention and a compatible pharmaceutical carrier to elicit the production of antibodies against said receptor. The appropriate amount of the SRTA-70 proteins which would be required would be known to one of skill in the art or could be determined by routine experimentation. SRTA-70 specific antibodies may also be selected from phage, viral, or bacterial antibody libraries. As used in connection with this invention the term "pharmaceutical carrier" can mean either the standard compositions which are suitable for human administration or the typical adjuvants employed in animal vaccinations.

Suitable adjuvants for the vaccination of animals include but are not limited to Freund's complete or incomplete adjuvant (not suitable for human or livestock use). Adjuvant 65 (containing peanut oil, mannide monooleate, aluminum phosphate and alum; surfactants such as hexadecylamine, octadecylamine, lysolecithin, dimethyldioctadecylammonium bromide, $N_1$-N-dioctadecyl-N'-N-bis(2-hydroxyethylpropanediamine), methoxyhexydecylglycerol, and pluronic polyols; polyanions such as pyran, dextran sulfate, poly IC, polyacrylic acid, carbopol; peptides such as muramyl dipeptide, dimentylglycine, tuftsin; and oil emulsions. The SRTA-70 proteins could also be administered following incorporation into liposomes or other microcarriers, or after conjugation to polysaccharides, other proteins or other polymers or in combination with Quil-A to form "Iscoms" (immuno-stimulating complexes) (Morein et al., Nature 308, 457 [1984]).

Typically, the initial vaccination is followed some weeks later by one or more "booster" vaccinations, the net effect of which is the production of high titers of antibodies against the SRTA-70 proteins which can be harvested in the usual way.

Another method consists in using the well-known Koehler and Milstein technique for producing monoclonal antibodies. In order to find out different monoclonal antibodies which are directed against the same antigen but against different epitopes, the method of Stähli et al. (J. of Immunological Methods 21, 297–304 [1980]) can be used.

The antibodies against the SRTA-70 proteins are useful for determination of the expression (over- and underexpression) of SRTA-70 protein. As set forth below altered features of SRTA-70 expression may lead to cancer and allergy.

Various methods which are generally known can be employed in the determination of SRTA-70 protein.

In one such procedure known amounts of a sample to be assayed, radio-labeled SRTA-70 protein and unlabeled SRTA-70 protein are mixed together and allowed to stand. The antibody/antigen complex is separated from the unbound reagents by procedure known in the art, e.g., by treatment with ammonium sulphate, polyethylene glycol, second antibody either in access or bound to an insoluble support, dextran-coated charcoal and the like. The concentration of the labeled SRTA-70 protein is determined in either the bound or unbound phase and the SRTA-70 content of the sample can then be determined by comparing the level of labeled component observed to a standard curve in a manner known per se.

Another suitable method is the "Double-Antibody-Sandwich-Assay". According to this assay the sample to be tested is treated with two different antibodies. One of these antibodies is labeled and the other is coated on a solid phase.

Suitable solid phases are organic and inorganic polymers [amylases, dextrans, natural or modified celluloses, polyacrylamides, agaroses, magnetite, porous glass powder, polyvinylidene fluoride (Kynar) and latex], the inner wall of test vessels (test tube, titer plates or cuvettes of glass or artificial material) as well as the surface of solid bodies (rods of glass and artificial material, rods with terminal thickening, rods with terminal lobes or lamellae). Spheres of glass and artificial material are especially suitable solid phase carriers.

Suitable labels are enzymes, e.g., peroxidase, radio-labels or fluorescence-labels.

Different antibodies can, e.g., be achieved by immunizing different animals, e.g., sheep and rabbits.

The methods for the determination of SRTA-70 protein as described above can be conducted in suitable test kits comprising in a container antibodies against SRTA-70 protein elicited by a SRTA-70 protein of the present invention.

The isolated DNA sequences encoding SRTA-70 proteins are useful to make probes for assaying the status of the natural SRTA-70 gene (i.e. mutations, deletions, rearrangements, amplifications etc.), or its expression (over- and underexpression). This could be relevant to class switch recombination, DNA recombination and repair in general, and other processes. There might be diseases, that are linked to altered features of SRTA-70, for example, DNA repair deficiencies leading to cancer; class switch aberrations or redirections towards allergy-causing IgE expression, and general B lymphocyte hypo- or hyperactivity.

The isolated DNA sequences encoding SRTA-70 proteins can also be used to generate antisense RNA to alter expression of the endogeneous SRTA-70 gene.

The isolated DNA sequences encoding SRTA-70 proteins, cloned into appropriate vectors, can be used for overexpression of the gene in target cells. This could create cellular models for the effect of altered SRTA-70 expression on class switch recombination, DNA recombination and repair, related processes, and general B cell function. This could allow to search for compounds which (counter-) regulate SRTA-70 protein expression.

Finally, the isolated DNA sequences encoding SRTA-70 proteins can be used to generate knockout mice. Such mice may have altered class switch recombination, and/or altered DNA recombination and repair processes in general. Such mice could be used as models for recombination-related diseases (cancer, allergies etc.), as well as for immune disorders related to B cell function, and as models for the respective therapeutic trials.

It has also been discovered that protein B23 has DNA recombination functions. Thus, the present invention provides in addition the use of protein B23 as a mediator of protein-protein interactions to retrieve other proteins involved in DNA recombination and repair, especially class switch recombination, and other DNA metabolic processes. Protein B23 could serve as a hook to pull other relevant proteins out of cell extracts. and allow cloning the respective genes. Protein B23 could also be used for screening of compounds inhibiting or boosting the function of B23 (agonists or antagonists) and proteins and nucleic acids interacting with B23.

Isolated DNA sequences encoding protein B23 are useful to make probes for assaying the status of the natural B23 gene (i.e. mutations, deletions, rearrangements, amplifications etc.), or its expression (over- and under-expression). This could be relevant to class switch recombination, DNA recombination and repair in general, and other processes. There might be diseases, that are linked to altered features of B23 (for example DNA repair deficiencies leading to cancer; class switch aberrations or redirections towards allergy-causing IgE expression).

Further it has been discovered that protein PARP interacts with proteins B23 and SRTA-70. Thus, the present invention provides further the use of protein PARP as a regulator of the recombinative (DNA metabolic) functions of B23 and SRTA-70 and thereby involvement of PARP through interaction with SRTA-70 and B23 in class switch recombination; DNA repair and recombination, and related processes.

Having now generally described this invention, the same will become better understood by reference to the specific examples, which are included herein for purpose of illustration only and are not intended to be limiting unless otherwise specified, in connection with the following figures:

BRIEF DESCRIPTION OF THE FIGURES

FIG. 1 is a schematic representation of the DNA transfer assay. The double-stranded (ds) M13 DNA contains Sγ and is digoxigenin-labeled; the pSP plasmid contains Sγ and is $^3$H labeled. The two substrates are coincubated with a nuclear extract, e.g., from switching B cells. DNA transfer from the Sγ plasmid to the Sμ plasmid results in plasmids containing both $^3$H and digoxigenin label. These plasmids can be precipitated by a bead-bound antibody to digoxigenin, washed, and their radioactivity measured in the scintillation counter.

FIG. 2 shows DNA transfer activity in extracts and extract fractions from switching and non-switching splenic cell populations. (A) Nuclear extract (Fraction I; 850 ng/reaction) and SRTA Fraction II (80 ng/reaction) tested with DNA substrates containing or lacking S-regions. (B) SRTA Fraction IV (1 ng/reaction) tested in two independent experiments (stippled and black boxes) with DNA substrate combinations containing either both S regions, one S region (pSP-Sγ) and an unrelated DNA (M13 RF, SV40, or ΦX174 RF), or no S regions (pSP+M13 RF) as indicated.

FIG. 3 shows analysis of switch recombination products. (A) PCR products were analyzed by Southern blotting and hybridization with either an Sμ or an Sγ probe as indicated. −T, without DNA templates; −P, no SRTA protein added; +P, complete reaction; −γ, Sγ substrate omitted from the recombination reaction. X Sγ, hybridized with Sγ, X Sμ, hybridized with Sμ. (B) Southern blot analysis of individually cloned PCR fragments obtained from DNA transfer reactions. M, size marker; γ and μ, plasmids containing Sγ and Sμ, respectively. X Sγ, hybridized with Sγ(3.7 kb EcoRI/HindIII fragment); X Sμ, hybridized with Sμ (1.3 kb HindIII fragment).

FIG. 4 shows the DNA sequence of the SRTA-70 gene (SEQ ID No:2) and the amino acid sequence of the SRTA-70 protein (SEQ ID No:1). Shaded regions indicate nuclear localization signals.

FIG. 5 shows protein interaction between B23, PARP, and SRTA-70. (A) Purification of overexpressed SRTA-70. His-tagged SRTA-70 (cDNA cloned into pQE-30; Quiagen Inc.) was isolated from IPTG-induced E.coli, purified on a Ni-agarose column (Fr. I), followed by a Superdex 200 gel filtration column (Fr. II). Un=uninduced, I=induced E.coli cell lysates (B and C). Protein fractions were eluted from the SRTA-70 affinity column at the indicated ammonium sulfate concentrations and probed in Western blots with (B) anti PARP antibody (Anwar Inc.), or (C) anti B23 antibody (Chan et al., J. Biol. Chem. 261, 14335 [1986]). Numbers at the top refer to mM ammonium sulfate used for elution.

FIG. 6 shows DNA dynamic activities of B23 protein. (A) Pairing of complementary DNA single-strands. A heat-denatured 422 bp, $^{32}$P end-labeled DNA fragment was incubated with various amounts of B23 protein, or E. coli RecA protein, or without protein (−), and in the presence or absence of ATP or MgCl$_2$ as indicated. The assay was performed as described in EMBO J. 15, 4061–4068 [1996]. ss, single-strand substrates, ds, double-strand reannealed product. (B) and (C) Formation of joined molecules in a D-loop assay as described. 1, product, 2, unspecific ds substrate band, 3, ss substrate. (B) Linear or supercoiled pSP-Sγ plasmid DNA and the $^{32}$P labeled ss oligonucleotide (Sγ, 49 nt) with or without B23 protein under various conditions as indicated. (C) The Sγ oligonucleotide was incubated with (50 or 100 ng) or without (−) B23 and either pSP-Sγ, pSP-Sμ or pSP plasmid DNA.

Figure 7:
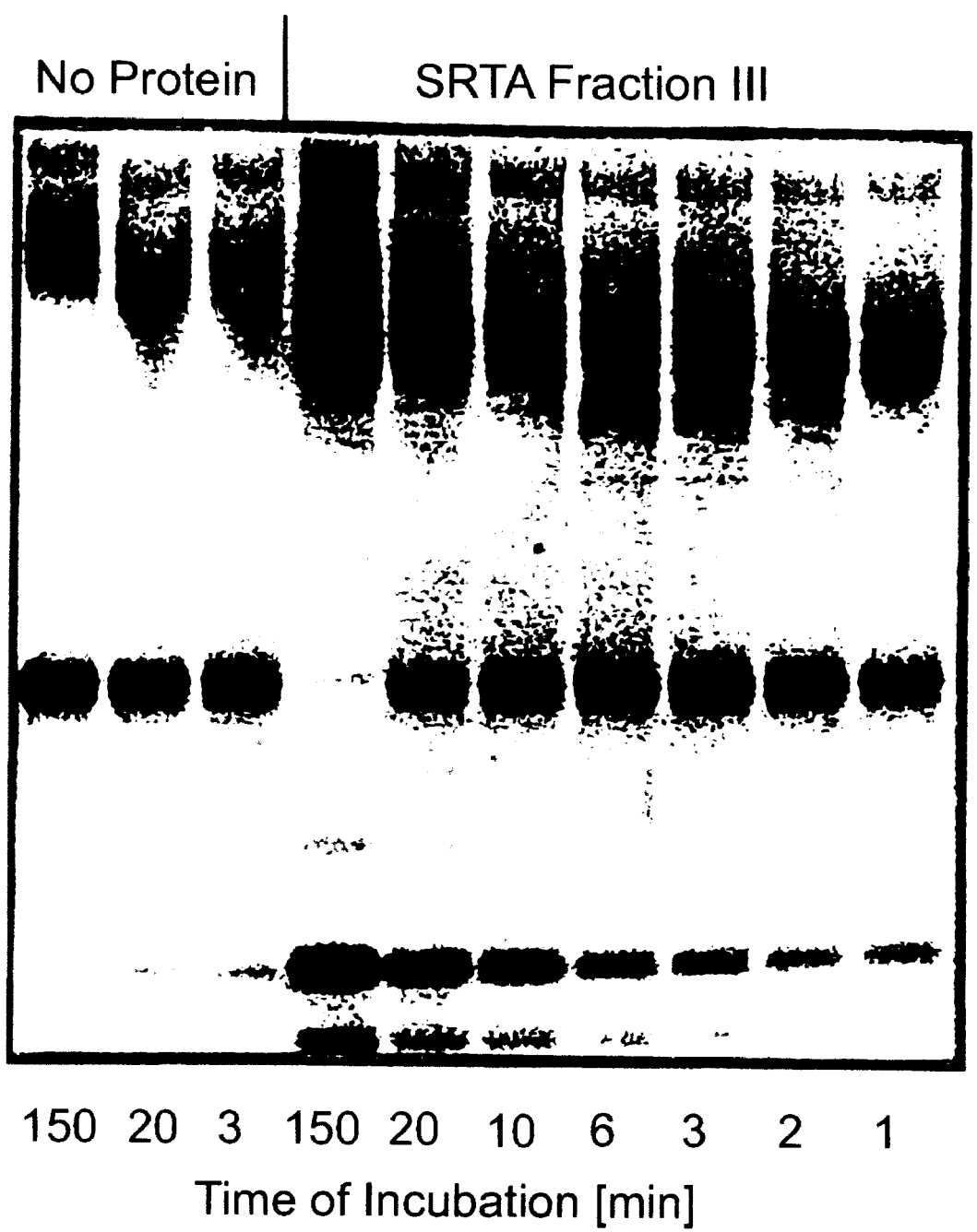

FIG. 7 shows endonuclease activity in SRTA. The ds M13-Sμ DNA (50 ng) was incubated for the times indicated with or without SRTA protein in the standard DNA transfer reaction buffer. After SDS/proteinase K treatment, products were analysed by gel electrophoresis (0.5% agarose, 0.5× TBE), Southern blotting, and hybridisation with $^{32}$P-labeled M13-Sμ DNA. Cleavage products (A, B) appear in the lower part of the gel.

Figure 8A:
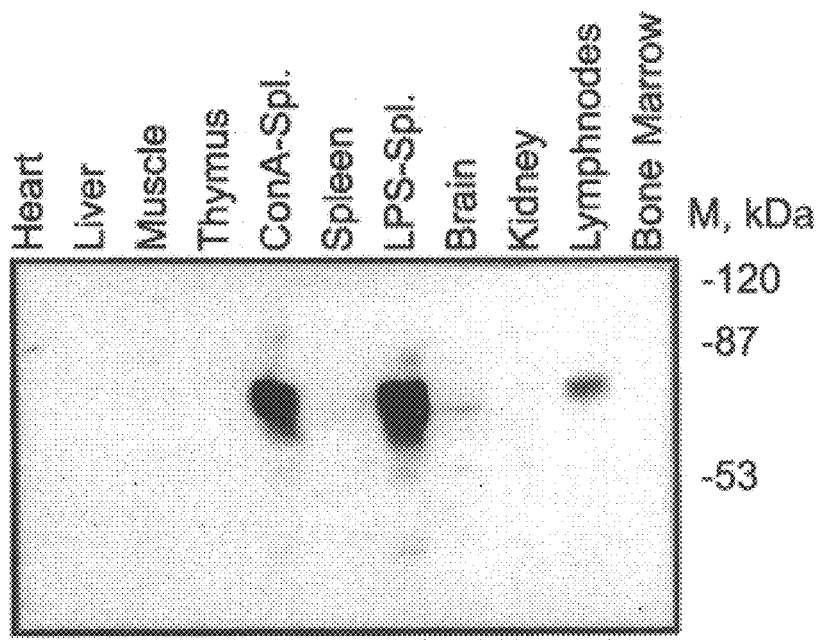
Figure 8B:
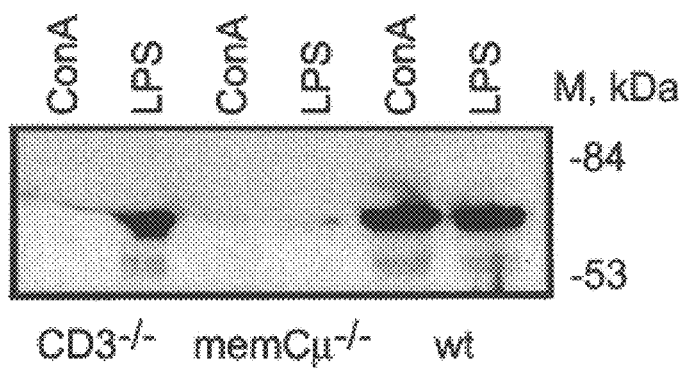

FIG. 8 shows activated B lymphocyte-specific expression of SRTA-70 protein. Nuclear extract protein from the various tissues and cells indicated was analysed by SDS-PAGE and immuno blotting using polyclonal rabbit anti-SRTA-70 antibodies (affinity-purified on a SRTA-70 affinity column).
LPS, lipopolysaccharide-stimulated cells
ConA, Concanavalin A stimulated cells
CD3$^{-/-}$, spleen cells from a CD3$^{-/-}$ mouse (no T-cells)
memCμ$^{-/-}$, spleen cells from a membrane Cμ-deficient mouse (no B-cells)
wt, wildtype.

EXAMPLE 1

Purification of SRTA-70

Plasmid pSP72 containing 2.1 kbp Sγ2b sequences was labeled with $^3$H-thymidine, and double-stranded (ds) M13 containing 1.3 kbp Sμ sequences was labeled with a small number of digoxigenin ligands. An S region preferring recombination activity should catalyse the formation of recombinant DNA molecules, of which one example is shown in FIG. 1, containing both labels. The amount of such molecules can be measured by counting $^3$H in plasmid DNA that has been immunoprecipitated by an anti-digoxigenin antibody.

Since splenic B cell cultures contain many different cell types, including a large portion of non-B lymphocytes and non-lymphocytic cells, lipopolysaccharide (LPS) stimulated (i.e. switching) B cell blasts were separated from the non-switching cells according to size by cell elutriation (Sanderson et al., Anal. Biochem. 71, 615–622 [1976]). Nuclear extracts were prepared as described (Jessberger and Berg, Mol. Cel.. Biol. 11, 445–457 [1991]), from 1×10$^8$ to 8×10$^8$ LPS (50 μg/ml) blasts (0.7 mg nuclear protein/10$^8$ cells). Nuclear extracts were tested for DNA transfer activities as described (Jessberger and Berg, supra). Input $^3$H radioactivity was between 150000 and 350000 cpm and the same for each experimental series. The Sμ substrate consisted of an M13 ds DNA carrying a 1.3 kbp HindIII Sμ fragment (DePinho et al., Mol. Cell. Biol. 4, 2905–291 [1984]), and was labeled with digoxigenin (Jessberger and Berg, supra). The Sγ plasmid consists of pSP72 containing a 3.7 kb Eco RI-HindIII Sγ2b fragment (De Pinho et al., Mol. Cell. Biol. 4, 2905–2912 [1984]); it was internally labeled with $^3$H-thymidine (Jessberger and Berg, supra). For the standard DNA transfer assay 0.18 μg of the $^3$H labeled DNA (e.g. pSP-Sγ) and 0.02 μg of the dig-labeled DNA (e.g. M13-Sμ) were coincubated with varying amounts of protein in 50 μl containing 3 mM MgCl$_2$, 30 mM EPPS, pH 7.4, 1 mM DTT, less than 50 mM ammonium sulfate, and 1 mM ATP. After 6 min the reaction was terminated by the addition of EDTA to 75 mM and SDS to 0.02% and heated to 65° C. for 20 min. The reaction mixture was extracted with phenol-chloroform (1:10) and incubated with anti digoxigenin beads (Jessberger and Berg, supra). The beads were collected on glass wool, washed with PBS-0.05% Tween-20, and the radioactivity of both the bead-bound and unbound DNA (together accounting for the total radioactivity) counted separately in a scintillation counter.

Figure 2A:
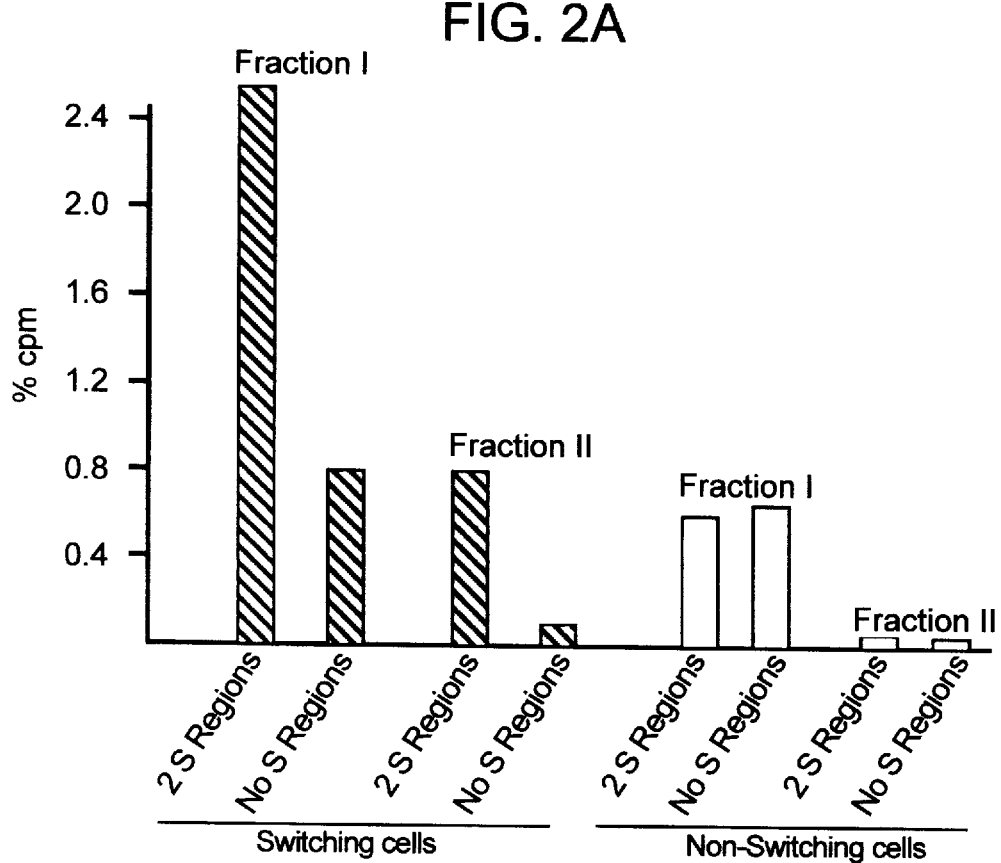

Despite the presence of general DNA transfer activities, the crude nuclear extracts from LPS blasts recombined S region substrates (SRS) two- to threefold better than non-S region substrates (NSRS), and this preference was not seen in extracts prepared in parallel from the non-switching splenic cell pool (FIG. 2A). This indicates induction of a new activity in switching cells.

Fraction I (2 mg protein) was loaded onto a Superdex 200 FPLC gel filtration column (Pharmacia) and fractionated at a flow rate of 1 ml/min in buffer E (5 mM KCl, 5 mM $MgCl_2$, 2 mM DTT, 0.2 mM EDTA, 15 mM Tris-HCl, pH 7.5 at 4° C., and 1 mM PMSF, 10 mM $Na_2S_2O_5$, 1 µg/ml aprotinin, 0.5 µg/ml TLCK, 0.7 µg/ml pepstatin A) containing 80 mM ammonium sulfate. 1.4 ml fractions were collected. Active fractions eluting around 57–61% column volume were pooled (5.6 ml, 0.6 mg protein, Fraction II), diluted 1:4 with buffer E and loaded at 1 ml/min onto a 1 ml Macro S cation exchange FPLC column (BioRad). After washing the column with 20 column volumes buffer E-20 (E plus 20 mM ammonium sulfate), the proteins were eluted at a 1 ml/min flow rate with a gradient from 20 to 600 mM ammonium sulfate in buffer E in 1.2 ml fractions. The switch-specific activity (2.4 ml, 0.011 mg protein, Fr. III) eluted in two fractions at around 280 mM ammonium sulfate. For further purification, Fraction III was diluted 1:2 with buffer E and loaded at 0.3 ml/min onto a 1 ml Blue-Sepharose (HiTrap, Pharmacia) FPLC column (pre-equilibrated in E-140). Elution was with a linear gradient from 0 to 1000 mM ammonium sulfate in buffer E, and the activity eluted between 740 and 810 mM (0.6 ml, 0.0006 mg protein, Fr. IV). On ice or at −70° C. the active fractions were stable for a short period only; frozen in liquid nitrogen, samples remained active for at least several weeks.

Figure 2B:
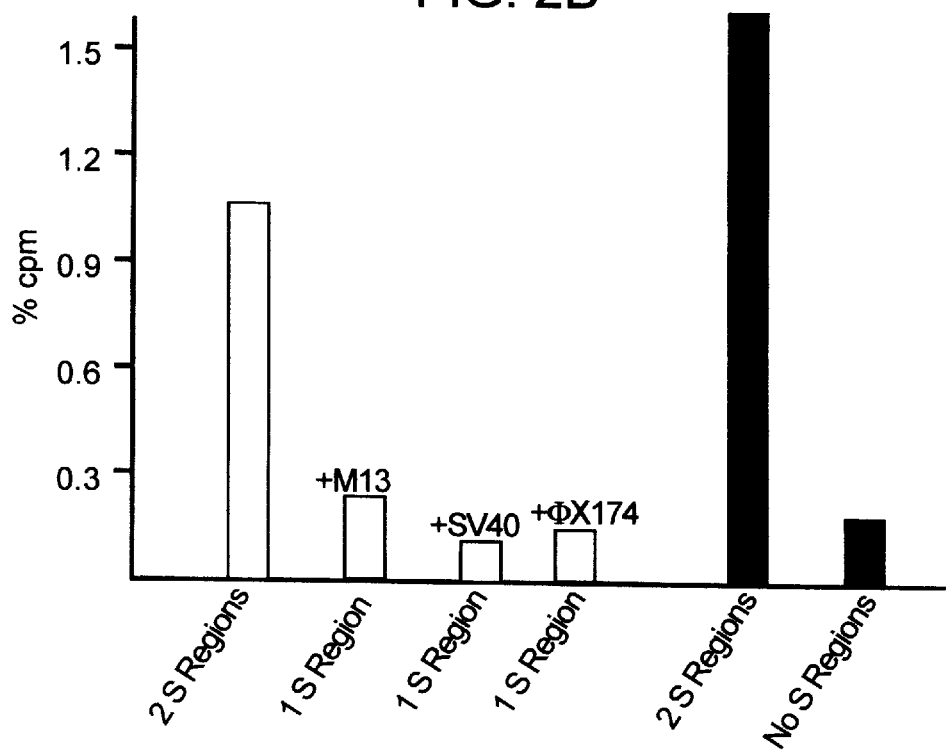

Fraction II showed an about 4 fold preference for SRS and was completely inactive if isolated from non-switching cells (FIG. 2A). The S region specific activity eluted at about 280 mM ammonium sulfate showed a nine-fold preference. Fraction IV the preference for S region substrates over non-S region substrated was about tenfold (FIG. 2B), with the non-S-substrates reaction yielding almost background levels of activity. With these purification steps the specific activity for DNA transfer between the S-substrates increased more than thousand-fold. Reactions that included one S region and an unrelated DNA like M13, SV40 or ΦX174 DNA as the second partner yielded low activity (FIG. 2B). Homologous DNA substrates (5.7 kbp homology) recombined with lower efficiency (app. 60%) than combinations of two SRS, as did substrates which shared limited homology (ca. 2 kbp stretch of homology; 45% efficiency) between them. Homology, therefore, is not sufficient to drive the reaction.

As maximum product formation by Fraction IV (1 ng) occurred after 6 min incubation at 37° C., and at 3 mM $MgCl_2$, these conditions were defined as standard conditions. Omission of the four dNTPs did not affect the reaction much (1.97%cpm versus 1.75%cpm of a standard reaction). In contrast, lack of ATP rendered the reaction 88% less efficient. When both the ATP and the four dNTPs were omitted, product formation was decreased to a similar degree (0.2%cpm versus 1.75%cpm of a standard reaction; and 0.2%cpm versus 1.97%cpm of the reaction lacking dNTPs). The dependence on ATP indicates energy cofactor requirement, but DNA synthesis seems not to be necessary, and no DNA polymerase activity was detected in Fractions III and IV; the fractions also lacked topoisomerase I and II, and DNA helicase activities.

Since the DNA was treated with SDS/EDTA and phenol, the linkage of the two substrates is considered stable and independent of the continuous presence of protein. More than 80% of the transfer products are heat stable (20 min at 85° C.).

In a next step, the structure of the recombination products was analyzed by PCR. Due to the imprecision of the switch recombination reaction and the possibility of multiple rearrangement events this analysis required special provisions. Thus, only the affinity-bead bound DNA was amplified which includes the digoxigenin-labeled substrate (M13-Sµ) and the DNA transfer products, but not the other substrate (pSP-S) DNA. The PCR primers were specific for S and Sµ and, thereby, diagnostic for junctions between two S regions. PCR reaction: Sµ-primer 5'-GATGGGTGGGCTTCTCTGAGCG (SEQ ID NO:3) (5' region of Sµ, bp. No. 67–88); S-primer 5'GTATTAGGGAC-CAGTCCTATCAG (SEQ ID NO:4) (middle of S, bp. No. 1076–1098); 1 min at 95° C. and 25 cycles of 20 s 95° C., 20 s at 50° C. and 1.1 min at 72° C. Amplification products were analyzed by Southern blot hybridization with either an S or an Sµ probe (FIG. 3A). As controls, the active protein (Fr. IV) or the DNA templates were omitted from the recombination reaction, or only one DNA substrate (Sµ) was used. Only when the DNA transfer reaction contained both DNA substrates together with the protein fraction did the products hybridize to both Sµ and S region probes (FIG. 3A). As expected from the imprecision of switch recombination, the observed products were heterogenous, though not entirely random, as the DNA transfer reaction and the PCR design may select for subsets of products. They also included Sµ-Sµ junctions. PCR products shown in FIG. 3A were subcloned into an unrelated plasmid vector and colony hybridization screens of cloned DNA were performed with either the S or Sµ probe. About 20% of the clones contained DNA hybridizing with both probes. The plasmids purified from the clones were linearized and Southern-hybridized with S and Sµ probes. As shown in FIG. 3B, seven of nine clones shown contained S and Sµ sequences of various sizes in the same molecule.

On silver stained SDS polyacrylamide gels there were 10 polypeptides left in Fraction III, and 6 polypeptides in Fraction IV. The prominent species in Fraction IV have approximate molecular weights of 38, 50, 70, 75, 115 and 160 kDa, respectively. The 38, 70, and 115 kDa proteins were gel-eluted and partial amino acid sequences of them were determined. Two tryptic peptides of the 38 kDa protein were TVSLGAG (SEQ ID NO: 5) and FINYVKI (SEQ ID NO: 6); of the 115 kDa protein TLGDFLAEYAK (SEQ ID NO: 7) and TTNFAGILSQG (SEQ ID NO: 8); and the N-terminal sequence of the 70 kDa protein was MRGLKDELLKAIWHAFTALDLDRS (SEQ ID NO: 9). The 38 kDa protein was identified as B23 (nucleophosmin; Chan et al., J. Biol. Chem. 261, 14335–14341 [1986]) and the 115 kDa protein as poly(ADP-ribose) polymerase (PARP; de Murcia and de Murcia, Trends Biochem. Sci. 19, 172–176 [1994]). The identifications were confirmed by Western blotting experiments. The complete sequence of the 70 kDa protein, named SRTA-70, is shown in FIG. 4. It does not belong to a known protein family and contains nuclear localization signals, a possible coiled-coil region between amino acids 320 and 450, a potential O-glycosylation site at amino acids 314/315, and a continuous hydrophilic region near its C-terminus.

EXAMPLE 2

Cloning of the DNA Sequence Encoding SRTA-70 and Expression and Purification of SRTA-70

The N-terminal amino acid sequence of SRTA-70 described in Example 1 was used to synthesize the oligonucleotides A and B, set forth below. These oligonucleotides correspond to either end of the N-terminal amino acid sequence of SRTA-70 and allow the generation of a RT-PCR product (72 bp) covering the entire N-terminal amino acid sequence of SRTA-70. From this 72 bp PCR product, an authentic 23 nt oligonucleotide was derived (see C below), which corresponds to the middle region of the N-terminal amino acid sequence of SRTA-70. The oligonucleotide C was then used as a $^{32}$P-labeled hybridization probe to screen a cDNA library (obtained from Stratagene Inc., mouse spleen cDNA library from 8–12 weeks old C57BL/6 female mice; Lambda ZAPII Vector; Catalog No. 936308). One positive clone was purified by three rounds of plaque purification (replating and hybridisation with C). It contained a 2.8 kbp insert spanning the entire SRTA-70 cDNA.

A: 5'-ATG MGN GGN YTN AAA GAC GA (SEQ ID NO: 10)

B: 5'-GT RAA NGC ATG CCA GAT (SEQ ID NO: 11)

C: 5'-GAA CTG CTC AAA GCC ATH TGC CA (SEQ ID NO: 12)

M=A or C, Y=C or T, N=A, T, G or C, R=A or G and H=A, C or T.

The SRTA-70 cDNA contained in the plasmid Bluescript in the Lambda vector was excised from the Lambda ZAPII Vector using the helper phage assisted excisison procedure given by Stratagene Inc. and using the material provided by Stratagene. The Bluescript-SRTA-70 clone DNA was then used as starting material for subcloning the cDNA into the pQE-30 vector (Quiagen Inc.) for expression of the his-tagged protein in *E. coli*. The cDNA was inserted into the Bam HI and EcoRV sites of the pQE-30 vector, transfected into the M15 *E. coli* host strain (Quiagen Inc.), and expression of the protein induced in positive clones by IPTG (1 mM) addition to the medium. Expression was monitored by SDS-PAGE analysis of *E. coli* cell extracts and Comassie staining. Clones that showed a strongly induced 70 kDa protein band were used for further analysis and larger scale expression. From these, cell lysates were prepared according to the following procedure:

cells were pelleted by centrifugation from the medium after 2 h induction in the presence of IPTG, and resuspended in ice-cold lysis buffer (50 mM Tris.HCl, pH 8.0, 300 mM NaCl, containing 1 tablet complete protease inhibitor unit from Boehringer Mannheim Inc., Cat. No. 1836153). Lysozyme was added to 2 mg/ml, and the cells incubated for 30 min. on ice. Imidazole and PMSF were added to 1 mM each, and the cell suspension was sonicated 5 times for 1 min until a viscous solution was generated. The insoluble fraction was removed by centrifugation (SS-34 rotor, Sorvall, 18000 rpm, 4° C., 20 min), and the clear supernatant, containing the SRTA-70 protein, collected.

This solution was then applied to a Ni-Agarose column for affinity chromatographic purification of the his-tagged SRTA-70, as suggested by the manufacturer (Quiagen Inc.). The column was washed with 10 volumes lysis buffer containing 1 mM Imidazole and then stepwise eluted with 20, 40, 80, 120, 200 mM Imidazole in the same buffer. The SRTA-70 protein eluted mainly in the 80 mM Imidazole step, as seen by SDS-PAGE analysis of the fractions. For further purification, this fraction was loaded on a Superdex 75 FPLC gel filtration column (Pharmacia), developed in a buffer containing 50 mM ammonium sulfate, 10% glycerol, protease inhibitors as above, 1 mM EDTA. The fractions containing SRTA-70 were frozen in aliquots in liquid niotrogen and stored at −70° C.

Figure 5A:
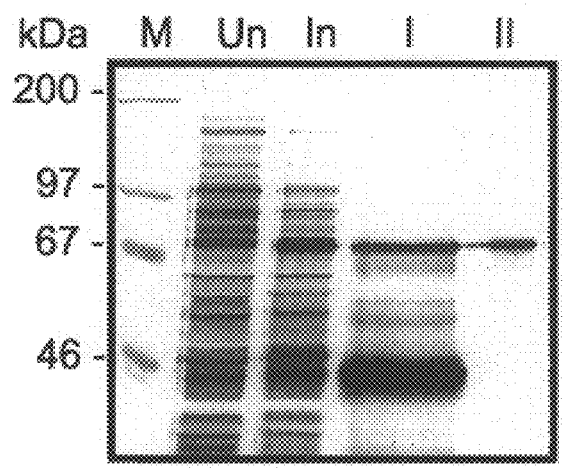
Figure 5B:
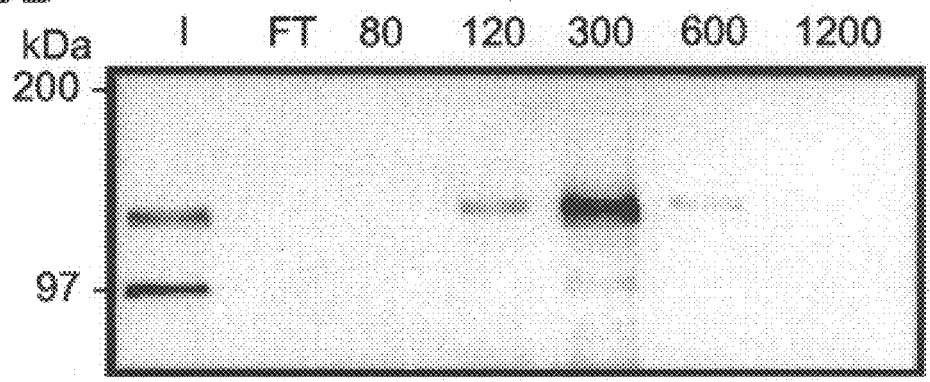
Figure 5C:
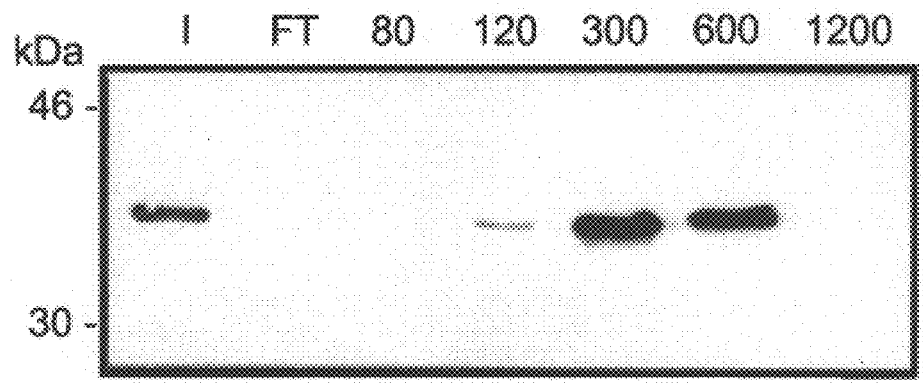

Expression and purification of SRTA-70 as a his-tagged molecule in *E. coli* yielded a >95% pure preparation (FIG. 5A, Frct. II). This preparation was used as an affinity-tag, bound to sepharose beads, for proteins contained in the nuclear extract from switching B cells. The bound material was stepwise eluted with 80, 120, 300, 600 and 1200 mM ammonium sulfate, and the fractions were analysed by SDS-PAGE and Western blotting. The 300, 600 and 1200 mM fractions contained only very few polypeptides, as judged from silver staind gels. Western blotting revealed PARP peaking in the 300 (FIG. 5B) and B23 peaking in the 300 and 600 mM fractions (FIG. 5C), corresponding to 600 and 1200 mM ionic strength, respectively, of a mono-valent salt. This indicated high affinity protein-protein interactions between B23, PARP, and SRTA-70.

EXAMPLE 3

Expression and Purification of Human SRTA-70

Human cDNA for SRTA-70 is cloned by using moderately degenerate PCR primer derived from the mouse cDNA sequence in a standard RT-PCR scheme (RT=Reverse Transcription). The human cDNA is alternatively cloned by the use of the one EST existing in the data bank (Accession No. W 39285) as a probe for screening human cDNA libraries. This EST is 89% homologous to the 3' end of the mouse SRTA-70.

EXAMPLE 4

Activities of B23 and PARP

Figure 6A:
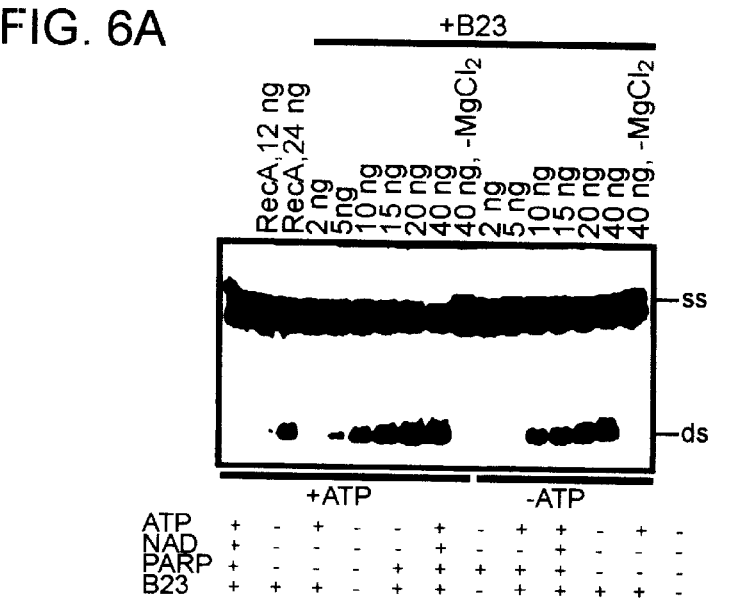

The ability of SRTA-70 and B23 to promote DNA pairing reactions was tested. Both proteins were overexpressed and purified from *E. coli* (FIG. 5A; Wang et al., J. Biol. Chem. 269, 30994–30998 [1994]). SRTA-70 was not active in the pairing assay, but B23 was at least as efficient as the *E. coli* RecA protein: 15 ng of B23 yielded as much double stranded (ds) DNA as 24 ng of RecA (FIG. 6A).

For a more complex three-strand pairing reaction—probably closer to the switch reaction—the formation of joined molecules generated by invasion of ss DNA into a ds target, the so-called D-loop formation (Kowalzykowski and Eggleston, Ann. Rev. Biochem. 63, 991–1043 [1994]; Beattie et al., J. Mol. Biol. 116, 783–803 [1977]) was tested.

25 fmoles predominantly supercoiled plasmid DNA and 0.6 pmoles (1.0 ng) 5'-32P labeled, 49 nt single-stranded S oligonucleotide (5' GGGACC AGTCCTAGCAGCTGT-GGGGGAGCTGGGGAAGGTGGGAGTGTGA) (SEQ ID NO: 13) were incubated together with protein for 30 min. at 37° C. in the standard DNA transfer reaction buffer. Reactions were stopped by addition of SDS to 0.1% and 4 μg Proteinase K and further incubation at 37° C. for 45 min. Products were analysed in 0.6% agarose gels containing 3 mM Mg-acetate in the TAE buffer system. Gels were run at 0.8 V/cm for 24 h at 4° C., stained with ethidium bromide, photographed, dried and exposed for autoradiography for 2–16 h.

Figure 6B:
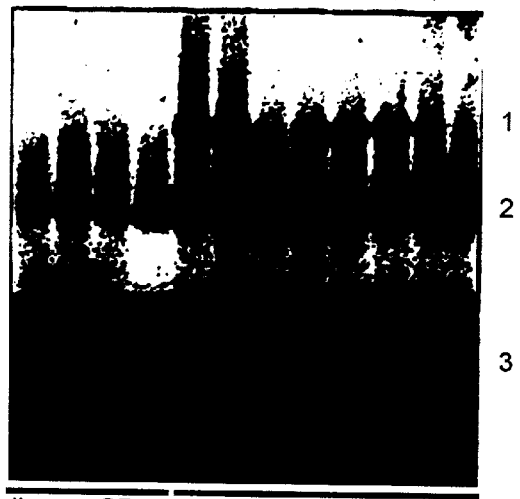

As seen in the four left lanes in FIG. 6B, linear plasmid DNA is not a substrate in the D loop reaction with 5'-$^{32}$P labeled single-strand oligonucleotide, as it is not in the reaction mediated by *E. coli* RecA (Beattie et al., supra). There is known unspecific, i.e., protein independent pairing, which probably is due to annealing of the oligonucleotide to partially and irreversibly denatured supercoiled DNA (band 2 in all lanes of FIG. 6B). During the specific reaction, however, the supercoiled substrate DNA is partially relaxed to the circular form, which constitutes the product (band 1). As shown in FIG. 6B, B23 transferred the 49 nt Sγ oligonucleotide into the predominantly supercoiled pSP-Sγ to produce band 1 in lanes 5, 6, 8, 9, and 10 (SRTA-70 was not active in this reaction). The activity of B23 is inhibited by the presence of 1 mM ATP (lane 11), but the inhibition can be overcome by inclusion of PARP in the reaction (lanes 6, 8, 9). PARP itself, however, is inactive in D-loop formation (FIG. 6B, lane 7). It is known that B23 can be modified by PARP and that it binds PAR polymers (Ramsamooi et al., Rad. Res. 143, 158–164 [1995]. The modification by PARP shown here does not depend on the presence of NAD (FIG. 6B, lanes 5, 8, 10) and thus could either be caused by direct protein-protein interactions, or by PAR polymers, present in the PARP preparation. ATP may inhibit B23 by occupying the polymer binding site, and may be competed out by the polymers. This mechanism might constitute a novel way to regulate B23 DNA dynamic activity. Indeed, in the SRTA fractions, about half of B23 was found in Western blotting experiments with anti PAR antibodies to contain the polymers.

Figure 6C:
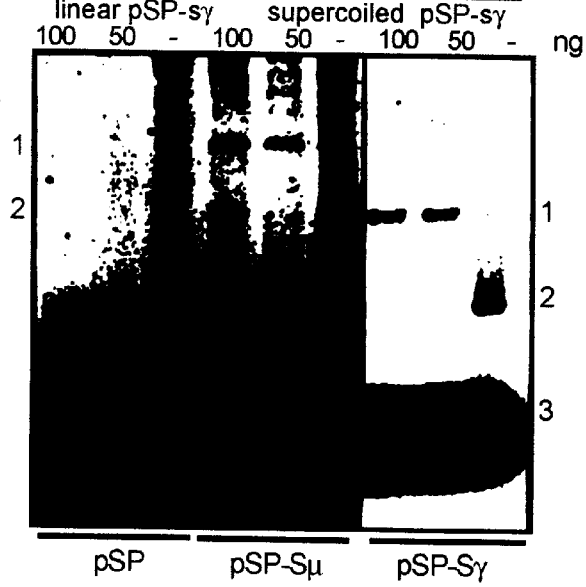

The homology between the 49 nt oligonucleotide and the pSP-Sγ target is to the best 92% over a 48 bp stretch. Since there exist patches of homologies between different S regions, it was tested for joined molecule formation with the Sγ oligonucleotide and a pSP-Sµ ds target DNA (FIG. 6C). The maximal homology here is 75% in a 48 bp stretch or 90% in a 11 bp stretch. Though not as efficient as the Sγ-Sγ pairing (right 3 lanes), B23 clearly was able to produce joined molecules with the two different S regions (middle 3 lanes). No joined molecules were obtained with the pSP plasmid DNA as target (left 3 lanes), although only slightly lower levels of homology exist (70–80% in stretches of 15–20 bp). Thus, small patches of homologies in the S regions may support pairing of different S regions but other sequence or structural elements, or a minimal length of stretches of homology as present in S regions are necessary to form stable products. B23 was also active in another three-strand reaction: DNA strand exchange between a linear, 3'-P32 labeled, 422 pb double-strand M13 DNA fragment and the single-strand, circular M13 phage DNA.

Although B23 can provide important DNA recombinative functions, it is not sufficient for the complete DNA transfer reaction, which requires the SRTA fraction. Among additional activities may be an endonucleolytic activity that initiates DNA transfer between two covalently closed circular DNA molecules. Such a requirement in switch recombination can also be deduced from the loop-excision model (Jäck et al., Proc.Natl., Acad. Sci. USA 85, 1581–1585 [1988]). Thus the SRTA was analysed for the presence of nuclease activities. These included 5'-3' ds exonuclease, 3'-5' ds exonuclease, ss endonuclease, ds endonuclease on linear DNA fragments, and ds endonuclease on predominantly supercoiled plasmid or phagemid DNA molecules. The only endonuclease detected cleaved supercoiled plasmid or phagemid DNA (FIG. 7). In Southern blotting of the product DNAs, the cleavage product appeared after 1–2 min incubation and increased thereafter. None of the other nuclease activities copurified with the SRTA. This DNA double-strand specific endonuclease did not depend on ATP or NAD, and is not a topoisomerase II activity, as this was absent from the preparation. The endonuclease was not specific for plasmids containing S regions. Secondary structures present in many plasmids and phagemids, and known to be formed by S regions may serve as cleavage signals. The cleavage products generated by this endonuclease might activate PARP, which depends on binding to DNA nicks or double-strand breaks (deMurcia and deMurcia, supra).

EXAMPLE 5

Expression of SRTA-70 Protein

Expression of SRTA-70 protein was investigated using standard immuno-blotting techniques and the antibodies mentioned above. A series of protein extracts from various tissues and either ConA- or LPS-stimulated spleen cells was probed (FIGS. 8A,B). High expression of SRTA-70 protein was found only in activated B lymphocytes.

What is claimed is:

1. An isolated polynucleotide comprising a DNA sequence having greater than 95% sequence identity to the nucleotide sequence set forth in SEQ ID NO:02, wherein said polynucleotide encodes an S-Region Transfer Activity-70 (SRTA-70) protein, wherein said SRTA-70 protein mediates recombination between immunoglobulin heavy chain switch regions.

2. The polynucleotide according to claim 1 comprising the nucleotide sequence set forth in SEQ ID NO: 2.

3. A vector comprising the polynucleotide as claimed in claim 1.

4. The vector as claimed in claim 3 wherein said vector is capable of directing expression in prokaryotic, yeast, plant, mammalian or insect host cells.

5. An isolated host cell comprising the vector as claimed in claim 3 wherein said host cell is selected from the group consisting of a prokaryote cell, a yeast cell, a plant cell, a mammalian cell and an insect cell.

6. The host cell of claim 5 which is a prokaryote cell.

7. A method for producing an SRTA-70 protein comprising cultivating a host cell as claimed in claim 5 in a suitable medium; and isolating said protein.

8. The polynucleotide of claim 1, wherein said SRTA-70 protein binds poly ADP ribose polymerase and B23.

9. An isolated SRTA-70 protein having an amino acid sequence greater than 95% sequence identity to the amino acid sequence set forth in SEQ ID NO:01, wherein said SRTA-70 protein mediates recombination between immunoglobulin heavy chain switch regions.

10. The protein according to claim 9, wherein said protein comprises an amino acid sequence as set forth in SEQ ID No: 1.

11. The SRTA-70 protein of claim 9, wherein said SRTA-70 protein binds poly ADP ribose polymerase and B23.

* * * * *

SEQUENCE LISTING

<160> NUMBER OF SEQ ID NOS: 13

<210> SEQ ID NO 1
<211> LENGTH: 585
<212> TYPE: PRT
<213> ORGANISM: Mus musculus

<400> SEQUENCE: 1

Met Arg Gly Leu Lys Asp Glu Leu Leu Lys Ala Ile Trp His Ala Phe
1               5                   10                  15

Thr Ala Leu Asp Leu Asp Arg Ser Gly Lys Val Ser Lys Ser Gln Leu
                20                  25                  30

Lys Val Leu Ser His Asn Leu Cys Thr Val Leu Lys Val Pro His Asp
            35                  40                  45

Pro Val Ala Leu Glu Glu His Phe Arg Asp Asp Asp Glu Gly Pro Val
        50                  55                  60

Ser Asn Gln Gly Tyr Met Pro Tyr Leu Asn Lys Phe Ile Leu Glu Lys
65                  70                  75                  80

Val Gln Asp Asn Phe Asp Lys Ile Glu Phe Asn Arg Met Cys Trp Thr
                85                  90                  95

```
Leu Cys Val Lys Lys Asn Leu Thr Lys Ser Pro Leu Leu Ile Thr Glu
                100                 105                 110
Asp Asp Ala Phe Lys Val Trp Val Ile Phe Asn Phe Leu Ser Glu Asp
            115                 120                 125
Lys Tyr Pro Leu Ile Ile Val Pro Glu Glu Ile Glu Tyr Leu Leu Lys
        130                 135                 140
Lys Leu Thr Glu Ala Met Gly Gly Gly Trp Gln Gln Glu Gln Phe Glu
145                 150                 155                 160
His Tyr Lys Ile Asn Phe Asp Asp Asn Lys Asp Gly Leu Ser Ala Trp
                165                 170                 175
Glu Leu Ile Glu Leu Ile Gly Asn Gly Gln Phe Ser Lys Gly Met Asp
            180                 185                 190
Arg Gln Thr Val Ser Met Ala Ile Asn Glu Val Phe Asn Glu Leu Ile
        195                 200                 205
Leu Asp Val Leu Lys Gln Gly Tyr Met Met Lys Lys Gly His Lys Arg
        210                 215                 220
Lys Asn Trp Thr Glu Arg Trp Phe Val Leu Lys Pro Asn Ile Ile Ser
225                 230                 235                 240
Tyr Tyr Val Ser Glu Asp Leu Lys Asp Lys Gly Asp Ile Leu Leu
                245                 250                 255
Asp Glu Asn Cys Cys Val Glu Ser Leu Pro Asp Lys Asp Gly Lys Lys
            260                 265                 270
Cys Leu Phe Leu Ile Lys Cys Phe Asp Lys Thr Phe Glu Ile Ser Ala
        275                 280                 285
Ser Asp Lys Lys Lys Gln Glu Trp Ile Gln Ala Ile Tyr Ser Thr
        290                 295                 300
Ile His Leu Leu Lys Leu Gly Ser Pro Pro His Lys Glu Ala Arg
305                 310                 315                 320
Gln Arg Arg Lys Glu Leu Arg Arg Lys Leu Leu Ala Glu Gln Glu Glu
            325                 330                 335
Leu Glu Arg Gln Met Lys Glu Leu Gln Ala Ala Asn Glu Asn Lys Gln
            340                 345                 350
Gln Glu Leu Glu Ser Val Arg Lys Lys Leu Glu Glu Ala Ala Ser Arg
        355                 360                 365
Ala Ala Asp Glu Glu Lys Lys Arg Leu Gln Thr Gln Val Glu Leu Gln
        370                 375                 380
Thr Arg Phe Ser Thr Glu Leu Glu Arg Glu Lys Leu Ile Arg Gln Gln
385                 390                 395                 400
Met Glu Glu Gln Val Ala Gln Lys Ser Ser Glu Leu Glu Gln Tyr Leu
                405                 410                 415
Gln Arg Val Arg Glu Leu Glu Asp Met Tyr Leu Lys Leu Gln Glu Ala
            420                 425                 430
Leu Glu Asp Glu Arg Gln Ala Arg Gln Asp Glu Thr Val Arg Lys
        435                 440                 445
Leu Gln Ala Arg Leu Leu Glu Glu Ser Ser Lys Arg Ala Glu Leu
        450                 455                 460
Glu Lys Trp His Leu Glu Gln Gln Ala Ile Gln Thr Thr Glu Ala
465                 470                 475                 480
Glu Lys Gln Glu Leu Gln Gln Arg Val Met Lys Glu Gln Ala Leu
                485                 490                 495
Gln Glu Ala Met Ala Gln Leu Glu Gln Leu Glu Leu Glu Arg Lys Gln
                500                 505                 510
Ala Leu Glu Gln Tyr Glu Gly Val Lys Lys Lys Leu Glu Met Ala Thr
```

-continued

```
        515                 520                 525
His Met Thr Lys Ser Trp Lys Asp Lys Val Ala His His Glu Gly Leu
            530                 535                 540

Ile Arg Leu Ile Glu Pro Gly Ser Lys Asn Pro His Leu Ile Thr Asn
545                 550                 555                 560

Trp Gly Pro Ala Ala Phe Thr Gln Ala Glu Leu Glu Glu Arg Glu Lys
                565                 570                 575

Ser Trp Lys Glu Lys Lys Thr Thr Glu
            580                 585

<210> SEQ ID NO 2
<211> LENGTH: 1758
<212> TYPE: DNA
<213> ORGANISM: Mus musculus

<400> SEQUENCE: 2
atgagggggt tgaaagacga actgctcaaa gccatttggc acgccttcac cgcgctcgac      60
ctggaccgca gcggcaaggt ctccaagtcg caactcaagg tcctttccca taacctgtgc     120
acggtgctga aggttccaca tgacccggtt gcccttgagg agcactttag ggatgacgat     180
gaggggcctg tctccaatca gggctacatg ccatatttaa acaagttcat tttggaaaag     240
gtccaagaca actttgacaa gattgaattc aatagaatgt gttggacact ttgtgtcaag     300
aaaaacctca caaagagtcc tctactcatt acagaagatg atgcatttaa agtgtgggtc     360
attttcaact ttttgtcaga ggacaagtat ccactaatta ttgtgccaga agagattgaa     420
tacctgctta agaagcttac agaagctatg ggaggaggtt ggcaacaaga acaatttgaa     480
cattacaaaa taaactttga tgacaataaa gatggccttt ctgcatggga acttattgag     540
ctaattggga atggacagtt tagcaagggc atggaccgtc agaccgtatc tatggccatt     600
aacgaagtct tcaatgagct tattttagat gtattgaagc agggttacat gatgaagaaa     660
ggtcacaaac ggaaaaactg gactgagcgc tggtttgtat taaaacccaa cataatttcc     720
tactatgtga gcgaggatct gaaagataag aaaggagaca tcctgctgga tgaaaactgc     780
tgtgtggagt ctctgcctga caaagatgga agaaatgtc tttttctaat aaaatgcttt     840
gataagacct ttgaaatcag tgcctcagat aagaagaaga acaagaatg gattcaggcc     900 atttactcca ccatccatct gttgaagctg gcagccccc caccacacaa ggaagcccgc     960
cagcgtcgga agagctccg aaggaagctg ctagccgagc aggaggagct ggagcggcag    1020
atgaaggaac tccaagccgc caatgaaaac aagcaacagg agctggaaag cgtgaggaag    1080
aaactggagg aagcagcctc tcgtgcggca gacgaggaaa agaaacgctt gcagactcag    1140
gtggagctac agaccaggtt cagcacggag ctggagcggg agaagctgat cagacagcag    1200
atggaggagc aggttgccca gaagtcctcc gaactggagc agtatctgca gcgagttcgg    1260
gagctggaag acatgtacct aaagctgcag gaggctcttg aggacgagag caggcccgg    1320 caggatgaag agactgtgcg caagcttcag gccaggttgc tggaggaaga gtcttctaag    1380
agggcagagc tggaaaagtg gcacctggag cagcagcagg ccattcagac aacagaggcg    1440
gagaagcagg agctggaaca gcagcgtgtc atgaaggagc aggcattgca ggaggccatg    1500
gcacagctgg aacagttgga gttggagcgg aagcaggccc tggagcagta tgagggagtt    1560
aaaaagaagc tagagatggc aacacatatg accaagagct ggaaggacaa agtggcccat    1620
catgagggat taatacgatt gatagaacca ggttccaaga accctcatct gatcaccaac    1680
tggggacccg cagcgttcac ccaggcagag ctcgaggaga gagagaagag ctggaaagag    1740
```
aagaagacca cagagtga                                                  1758

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gatgggtggg cttctctgag cg                                             22

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gtattaggga ccagtcctat cag                                            23

<210> SEQ ID NO 5
<211> LENGTH: 7
<212> TYPE: PRT
<213> ORGANISM: Mus musculus

<400> SEQUENCE: 5

Thr Val Ser Leu Gly Ala Gly
1               5

<210> SEQ ID NO 6
<211> LENGTH: 7
<212> TYPE: PRT
<213> ORGANISM: Mus musculus

<400> SEQUENCE: 6

Phe Ile Asn Tyr Val Lys Ile
1               5

<210> SEQ ID NO 7
<211> LENGTH: 11
<212> TYPE: PRT
<213> ORGANISM: Mus musculus

<400> SEQUENCE: 7

Thr Leu Gly Asp Phe Leu Ala Glu Tyr Ala Lys
1               5                   10

<210> SEQ ID NO 8
<211> LENGTH: 11
<212> TYPE: PRT
<213> ORGANISM: Mus musculus

<400> SEQUENCE: 8

Thr Thr Asn Phe Ala Gly Ile Leu Ser Gln Gly
1               5                   10

<210> SEQ ID NO 9
<211> LENGTH: 24
<212> TYPE: PRT
<213> ORGANISM: Mus musculus

<400> SEQUENCE: 9

```
Met Arg Gly Leu Lys Asp Glu Leu Leu Lys Ala Ile Trp His Ala Phe
 1               5                  10                  15
Thr Ala Leu Asp Leu Asp Arg Ser
             20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: n = A,T,C or G
<220> FEATURE:
<221> NAME/KEY: misc_feature
<222> LOCATION: (1)...(20)
<223> OTHER INFORMATION: m=A or C

<400> SEQUENCE: 10
atgmgnggny tnaaagacga                                          20

<210> SEQ ID NO 11
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: (1)...(17)
<223> OTHER INFORMATION: r=A or G

<400> SEQUENCE: 11
gtraangcat gccagat                                             17

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(23)
<223> OTHER INFORMATION: h=A,C or T

<400> SEQUENCE: 12
gaactgctca aagccathtg cca                                      23

<210> SEQ ID NO 13
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 13
gggaccagtc ctagcagctg tgggggagct ggggaaggtg ggagtgtga          49